(12) United States Patent
Baumgartner et al.

(10) Patent No.: US 9,144,688 B2
(45) Date of Patent: Sep. 29, 2015

(54) SYSTEMS AND METHODS FOR WIRELESS PAIRING AND COMMUNICATION FOR ELECTRO-STIMULATION

(71) Applicant: EMPI, INC., Vista, CA (US)

(72) Inventors: Flavien Baumgartner, Vevey (CH); Stéphane Perroud, Vullierens (CH); Philippe Vuadens, Blonay (CH); Nicolas Fontaine, Bottens (CH)

(73) Assignee: EMPI, INC., Vista, CA (US)

( * ) Notice: Subject to any disclaimer, the term of this patent is extended or adjusted under 35 U.S.C. 154(b) by 0 days.

(21) Appl. No.: 14/077,325

(22) Filed: Nov. 12, 2013

(65) Prior Publication Data

US 2014/0135880 A1    May 15, 2014

Related U.S. Application Data

(60) Provisional application No. 61/725,190, filed on Nov. 12, 2012.

(51) Int. Cl.
| | | |
|---|---|---|
| *A61N 1/00* | (2006.01) | |
| *A61N 1/372* | (2006.01) | |
| *H04W 4/20* | (2009.01) | |
| *H04W 84/20* | (2009.01) | |
| *H04L 29/08* | (2006.01) | |

(52) U.S. Cl.
CPC .......... *A61N 1/37288* (2013.01); *A61N 1/37247* (2013.01); *H04L 67/12* (2013.01); *H04W 4/206* (2013.01); *H04W 84/20* (2013.01)

(58) Field of Classification Search
USPC ...................................... 607/30, 60
See application file for complete search history.

(56) References Cited

U.S. PATENT DOCUMENTS

| | | |
|---|---|---|
| 4,941,201 A | 7/1990 | Davis |
| 5,016,634 A | 5/1991 | Vock et al. |
| 5,113,859 A | 5/1992 | Funke |
| 6,600,902 B1 | 7/2003 | Bell |
| 6,847,844 B2 | 1/2005 | Sun et al. |
| 7,088,233 B2 | 8/2006 | Menard |
| 7,138,902 B2 | 11/2006 | Menard |

(Continued)

FOREIGN PATENT DOCUMENTS

| | | |
|---|---|---|
| WO | WO 2007/081284 | 7/2007 |
| WO | WO 2012/117306 | 9/2012 |

OTHER PUBLICATIONS

International Search Report dated Nov. 12, 2013 received in International Application No. PCT/US2012/069546.

*Primary Examiner* — Nicole F Lavert
(74) *Attorney, Agent, or Firm* — Knobbe Martens Olson & Bear LLP

(57) ABSTRACT

The disclosure herein is directed toward systems and methods for pairing two or more devices into a wireless network and transferring data between two or more electro-stimulation devices. Specifically, the systems and methods disclosed herein may include pairing two or more devices into a network configuration using, in part, a pairing device to distinctly identify the devices to be paired and to pair the identified devices into a network. Moreover, the systems and methods disclosed herein may include transferring data between two or more devices using, in part, one or more electro-stimulation contacts for electro-stimulation therapy and using, in part, the same one or more electro-stimulation contacts for transferring data between two or more devices.

20 Claims, 15 Drawing Sheets

(56) References Cited

U.S. PATENT DOCUMENTS

| | | |
|---|---|---|
| 7,289,852 B2 | 10/2007 | Helfinstine et al. |
| 7,512,448 B2 | 3/2009 | Malick et al. |
| 7,777,641 B2 | 8/2010 | Karunasiri et al. |
| 8,059,573 B2 | 11/2011 | Julian et al. |
| 8,078,742 B2 | 12/2011 | Blackwell et al. |
| 8,082,160 B2 | 12/2011 | Collins, Jr. et al. |
| 8,254,992 B1 | 8/2012 | Ashenbrenner et al. |
| 8,315,705 B2 | 11/2012 | Keuninckx |
| 2008/0166968 A1* | 7/2008 | Tang et al. .................. 455/41.2 |
| 2009/0216296 A1 | 8/2009 | Meskens |
| 2009/0280745 A1 | 11/2009 | Granqvist et al. |
| 2010/0203829 A1 | 8/2010 | Granqvist et al. |
| 2011/0184492 A1 | 7/2011 | Martens et al. |
| 2012/0009875 A1 | 1/2012 | Miettinen et al. |
| 2012/0059436 A1 | 3/2012 | Fontaine et al. |
| 2012/0101874 A1 | 4/2012 | Ben-Haim et al. |
| 2012/0287984 A1 | 11/2012 | Lee |
| 2013/0337739 A1 | 12/2013 | Bernsen et al. |

* cited by examiner

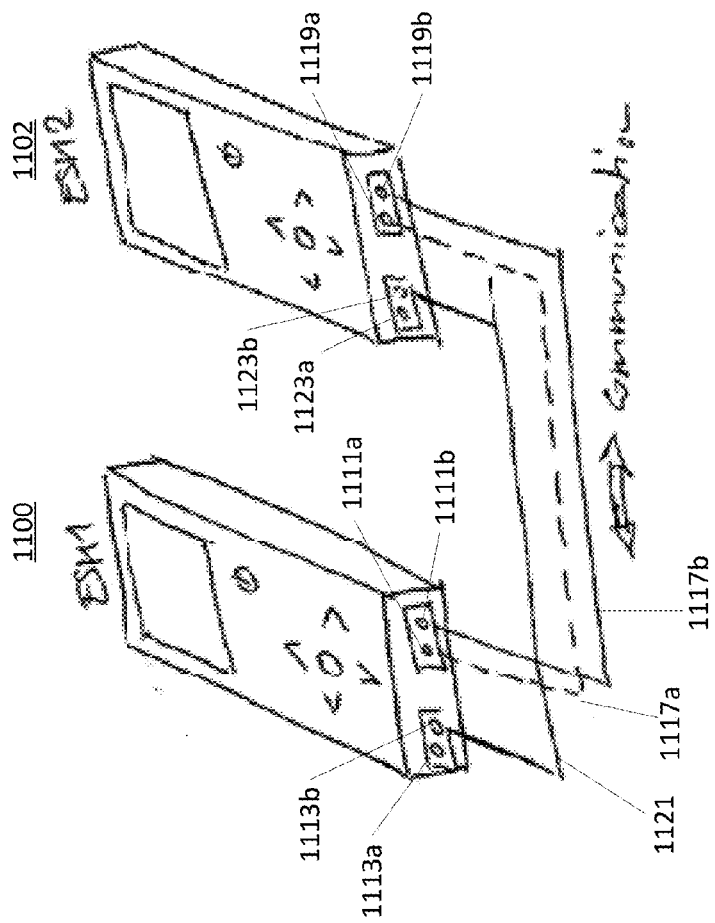
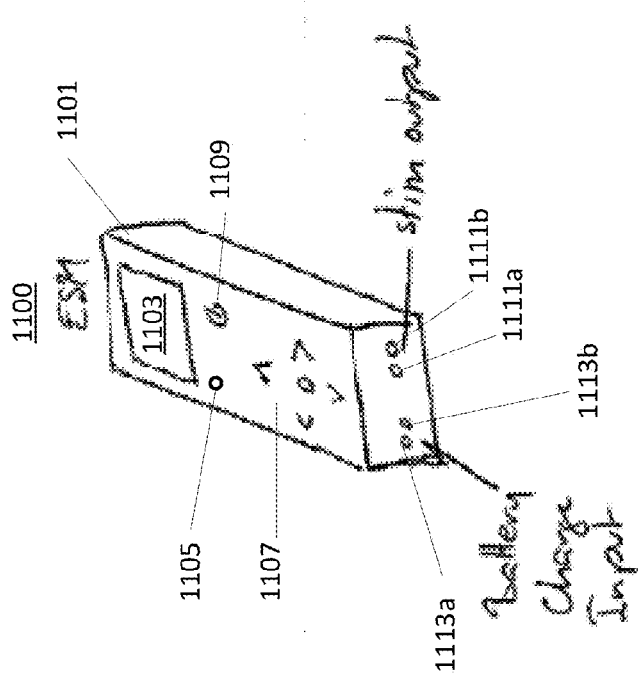
Figure 11B
Figure 11A ness one master and a slave. The communication between the additional device and the at least two devices may be made through wireless communication. Yet in other implementations, the wireless communication may be a magnetic coupling or Radio Frequency. The additional device may automatically recognize the presence of the other devices without any additional action from a user. In one implementation, the additional action from a user is an action on an actuator. The actuator may be a button. In another implementation, the pairing process is initiated by a user action. In some implementations, one of the at least two devices is an electro-stimulator device, a therapeutic ultrasound device, an imaging ultrasound device, or a laser device. The user interface of the device may be embedded in another device. Moreover, in other implementations, the pairing process remains permanent until another pairing process is initiated by a user.

SYSTEMS AND METHODS FOR WIRELESS PAIRING AND COMMUNICATION FOR ELECTRO-STIMULATION

REFERENCE TO RELATED APPLICATIONS

This application claims the benefit of U.S. Provisional Patent Application Ser. No. 61/725,190, filed Nov. 12, 2012, the disclosure of which is incorporated herein in its entirety.

TECHNICAL FIELD

The systems and methods described herein relate to wireless devices and medical devices. Specifically, the systems and methods relate to pairing two or more devices into a wireless network and transferring data between the two or more electro-stimulation devices.

INTRODUCTION

Traditional systems designed to pair devices into a wireless network use an intermediate network—each device to be paired, independently of the other devices, must locate and establish a connection with the intermediate network. A device typically pairs with other devices after each device has established a connection to the intermediate network. This approach works well in instances where a reliable intermediate network is available; however there remains the need for a method of pairing devices where an intermediate network is not available. There is also a need for a system that selectively identifies which devices, of the set of the available devices, to pair with or not to pair with, rather than pairing with all of the available devices.

Traditional systems designed to transfer data between two or more electro-stimulation devices use two different sets of electrical contacts—one set of electrical contacts is used for electro-stimulation therapy and the other set of electrical contacts is used for transferring data between the two or more devices. Typically, one set of wires connects the electro-stimulation contacts to the patient for electro-stimulation therapy and another set of wires connects the two or more devices via the data contacts for data transfer. This approach works well when the number of electrical contact and connectors is unimportant. However, there remains the need for a system that reduces the number of electrical contacts and the number of connectors and still provides electro-stimulation therapy and data transfer between two or more electro-stimulation devices. Specifically, there is a need for a system that uses one set of electrical contacts for providing electro-stimulation therapy and uses the same set of electrical contacts for transferring data between two or more devices.

SUMMARY

The systems and methods disclosed herein are for pairing two or more devices into a network. In some implementations, the system comprises at least two electronic devices, wherein at least one of the electronic devices communicates wirelessly with at least one of the other electronic devices; an additional device being configured to communicate with the at least two electronic devices, wherein the additional device communicates with the electronic devices for grouping the electronic devices into a wireless network. In one implementation, the additional device is a charging station. In other implementations, the communication between the additional device and the at least two electronic devices is made through electrical contact. In another implementation, the wireless Systems and methods are also disclosed herein for transferring data between two or more devices. In some implementations, the system comprises at least two devices, each of the at least two devices having an output with at least two electrical contacts, wherein the at least two devices deliver a therapy signal through the output, wherein the at least two electrical contacts are used to transfer data to another device. In one implementation, the output delivers an electro-stimulation therapy treatment. Other implementations may further comprise an electrically conductive component to connect the at least two devices. The electrically conductive component may be an electrical wire, human skin, or a charging station.

In other implementations, the system comprises at least two devices, each of the at least two devices comprising at least two electrical contacts, wherein at least one of the contacts is used to transfer data to another device, and wherein the at least one of the contacts is used for a function other than the data transfer. In some implementations the electrical contacts are battery charging inputs.

The systems and methods disclosed herein may pair two or more devices into a network configuration by using, in part, a pairing device to distinctly identify the devices to be paired and to pair the identified devices into a network. For example, the pairing device may use a proximity threshold to identify the devices to be paired. In addition, the pairing device may use a network communication protocol to pair the identified devices into a network. In some implementations, the pairing device does not rely on an intermediate network and operates even where an intermediate network is not available. In some implementations, the pairing device does not pair devices that are not identified to be paired and may reduce the likelihood that unintended pairings.

In addition, the systems and methods disclosed herein transfer data between two or more devices. The system may use one or more electro-stimulation contacts for electro-stimulation therapy from a device and may use the same one or more electro-stimulation contacts for transferring data between two or more devices. In addition, the system may use one or more battery charge contacts for providing power to a device and may use the same one or more battery charge contacts for providing a ground while transferring data between two or more devices.

Other objects of the invention will, in part, be obvious, and, in part, be shown from the following description of the systems and methods shown herein.

BRIEF DESCRIPTION OF THE DRAWINGS

The foregoing and other objects and advantages will be appreciated more fully from the following further description thereof, with reference to the accompanying drawings wherein:

FIG. 11A depicts an electro-stimulation (ESM) device including a stimulation output system and a battery charge input system;

FIG. 11B depicts electro-stimulation (ESM) devices, each including a stimulation output system and a battery charge input system, configured according to an implementation of a system that transfers data between two or more medical devices;

DESCRIPTION OF THE ILLUSTRATED IMPLEMENTATIONS

To provide an overall understanding of the teachings of this application, certain illustrative implementations will now be described, including a system that pairs at least two devices into a wireless network and a system that transfers data between two or more medical devices. However, it will be understood by one of ordinary skill in the art that the systems and methods described herein can be adapted and modified for other suitable applications, including combinations of such systems and methods, and that such other additions and modifications will not depart from the scope hereof.

The systems and methods disclosed herein pair two or more devices into a wireless network configuration by using, in part, a pairing device to distinctly identify the devices to be paired and to pair the identified devices into a wireless network. For example, the pairing device may use a proximity threshold to identify the devices to be paired. In addition, the pairing device may use, in part, a network communication protocol to pair the identified devices into a network. In some implementations, the pairing device does not rely on an intermediate network for pairing devices within a family. In some implementations, the pairing device selectively pairs particular devices in a group of devices and therefore can reduce the likelihood of unintended pairings.

In addition, the systems and methods disclosed herein comprise transferring data between two or more devices. The system may use one or more electro-stimulation contacts to provide electro-stimulation therapy from a device and may use the same one or more electro-stimulation contacts to provide data transfer between two or more devices. In addition, the system may use one or more battery charge contacts to provide power to a device and may use the same battery charge contacts to provide a ground during data transfer between two or more devices.

Figure 1:
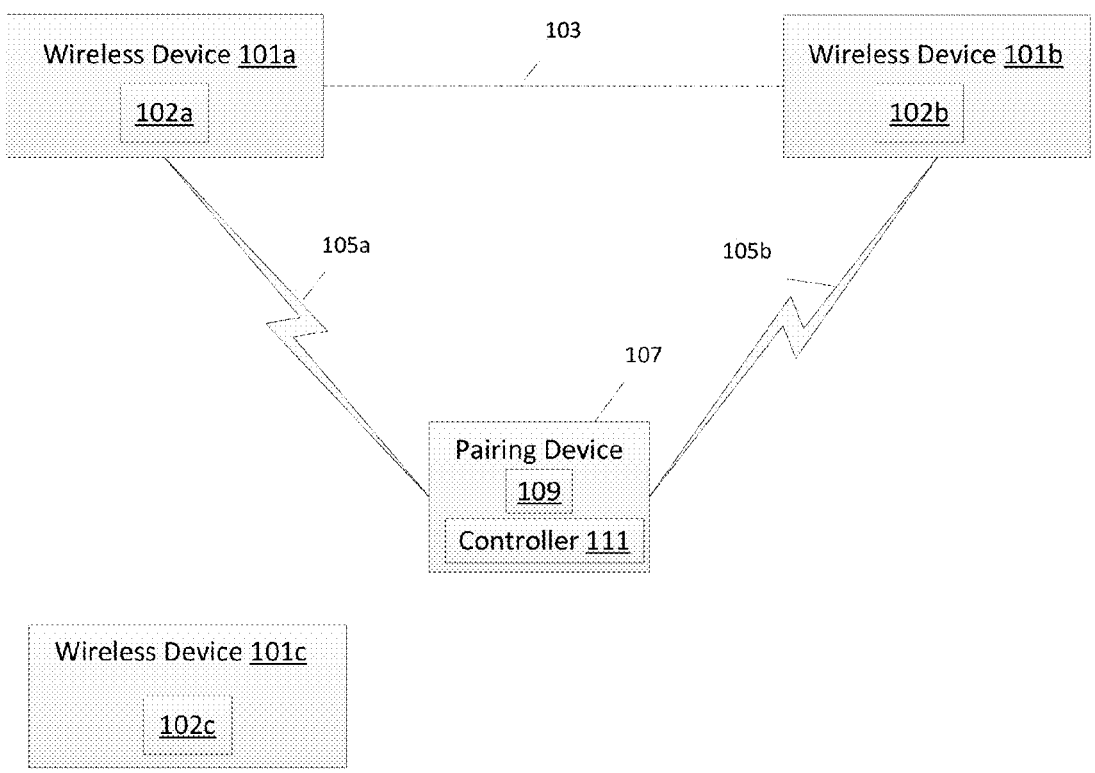
FIG. 1 depicts the structure of an implementation of a system that pairs at least two devices into a wireless network.

FIG. 1 depicts a system 100 for pairing at least two devices into a wireless network. System 100 may include a set of at least two wireless devices 101a, 101b, and 101c, pairing device 107, communication link 105 and communication link 103. Wireless devices 101a, 101b, and 101c may contain communication systems 102a, 102b, and 102c configured with circuitry to communicate with other devices like, for example, devices 101 and 107 through communication link 103 and communication links 105a and 105b, respectively. Pairing device 107 contains controller 111, which is connected to communication system 109. Controller 111 may contain a microprocessor (not shown) to process, read, store, or modify data or instructions between the components of system 100. Communication system 109 is configured with circuitry to communicate with devices like, for example, wireless devices 101a, 101b, and 101c through communication links 105a and 105b.

In one implementation, wireless devices 101a and 101b communicate with each other through communication link 103 only after they have identified themselves to each other through communication links 105a and 105b using pairing device 107. For example, wireless devices 101a and 101b may be assigned a unique identification number during their manufacturing process (unique ID). The pairing process may include sharing the unique ID of each device to be paired with each other device to be paired using, for example, communication link 105a and 105b. Paired devices are able to identify each other and to communicate via, for example, communication link 103 after each device to be paired has been delivered the unique ID of each other device to be paired. In FIG. 1 wireless devices 101a and 101b are paired through communication link 105a and 105b and therefore are able to communicate with each other through communication link 103. Pairing device 107 groups, or pairs, wireless devices 101a and 101b into a wireless network. In some implementations, the pairing process remains permanent until another pairing process is initiated by the user. Wireless device 101c is not paired to wireless devices 101a and 101b and therefore is not in the same wireless family and may not communicate with the wireless devices 101a and 101b through communication link 103 or from a similar link. In one implementation, pairing system 100 includes two or more wireless devices 101a, 101b, and 101c; three wireless devices are shown in FIG. 1 for illustrative purposes only.

In some implementations, wireless devices 101a, 101b, and 101c, may include a medical device system that is enabled with a wireless communication system. For example, wireless device 101a, may be an electro-stimulation unit (e.g. TENS), and wireless devices 101b and 101c may be electrodes. Wireless devices 101 may be at least two electronic devices that are able to wirelessly communicate with each other. In other implementations, one or more of wireless devices 101 is a master device, and one or more of wireless devices 101 may be a slave device. The pairing process may include each of the at least one master devices sharing its unique ID with each of the at least one slave devices, while each of the at least one slave devices shares its unique ID with each of the least one master devices. In general, wireless devices 101 may be any device with a suitable wireless communication system. In some implementations, communication link 105 is a wireless system, an electrical contact system, a magnetic coupling system, a Radio Frequency system, or may be any suitable system that allows pairing device 107 to communicate with wireless devices 101. Communication link 103 may be a radio frequency system, a wireless communication system, Wi-Fi, Bluetooth, Zigbee or may be any suitable communication system that allows wireless device 101a to communicate with wireless device 101b. In some implementations, pairing device 107 is a charging station. In other implementations, pairing device 107 can recognize the presence of other devices without any action from a user.

In other implementations, wireless devices 101a and 101b are assigned a unique identification number during their manufacturing process (unique ID). The pairing process, in part, includes sharing the unique ID of each device to be paired with each other device to be paired. In implementations that include at least one master device and at least one slave device, each of the at least one master devices may share its unique ID with each of the at least one slave devices, while each of the at least one slave devices may share its unique ID with each of the least one master devices.

Figure 2:
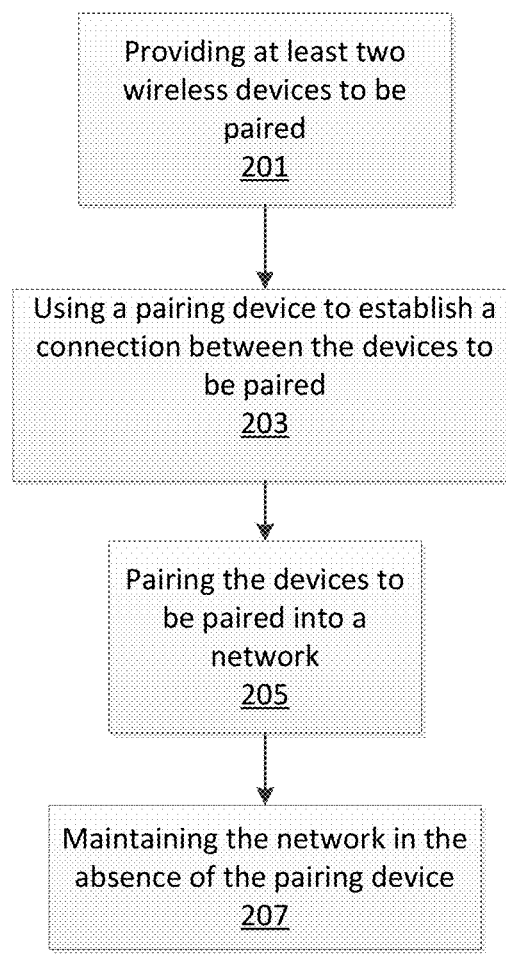
FIG. 2 illustrates a method for pairing at least two devices into a wireless network.

FIG. 2 illustrates of a method for pairing at least two devices into a wireless network. Method 200 includes the step 201 providing at least two wireless devices to be paired, step 203 using a pairing device to establish a connection between the devices to be paired, step 205 pairing the devices to be paired into a network, and step 207 maintaining the network in the absence of the pairing device. In some implementations, step 203 has the steps of providing a pairing device that can communicate with the device to be paired. Step 203 may include the step of placing the devices to be paired in contact with the pairing device. In other implementations, the network that is created as a result of step 205 remains permanent until another pairing process is initiated.

Figure 3:
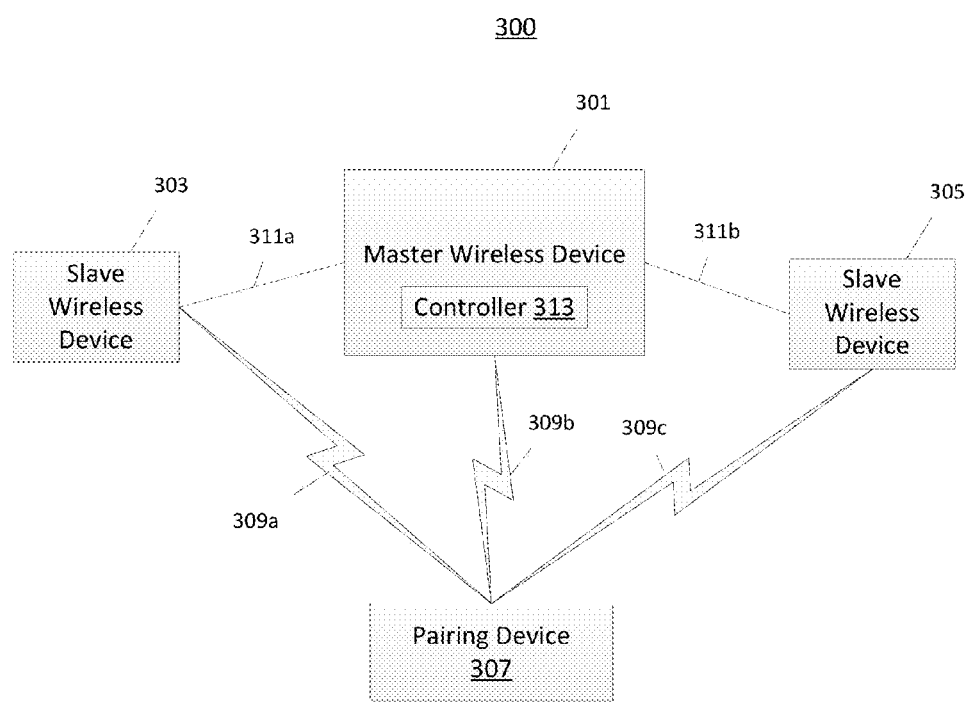
FIG. 3 depicts a master device and two slave devices configured according to an implementation of a system that pairs at least two devices into a wireless network.

FIG. 3 depicts a master device and two slave devices configured according to an implementation of a system that pairs at least two devices into a wireless network. System 300 contains master wireless device 301, set of slave devices 303 and 305, and pairing device 307. Master wireless device 301 contains a controller 313 that may contain a microprocessor (not shown) to process, read, store, or modify data or instructions between the components of system 300. In some implementations, master wireless device 301 sends signals through communication system 311a and 311b to control slave devices 303 and 305. Slave wireless devices 303 and 305 may be able to send and receive communications through communication system 311a and 311b to master wireless device 301. In some implementations, slave wireless devices 303 and 305 are not able to communicate with master wireless device 301. Pairing device 307 may be a stand-alone device or may be integrated with another device. For example, pairing device 307 may be implemented as a docking station, a charging and docking station, or a storage device.

Figure 4:
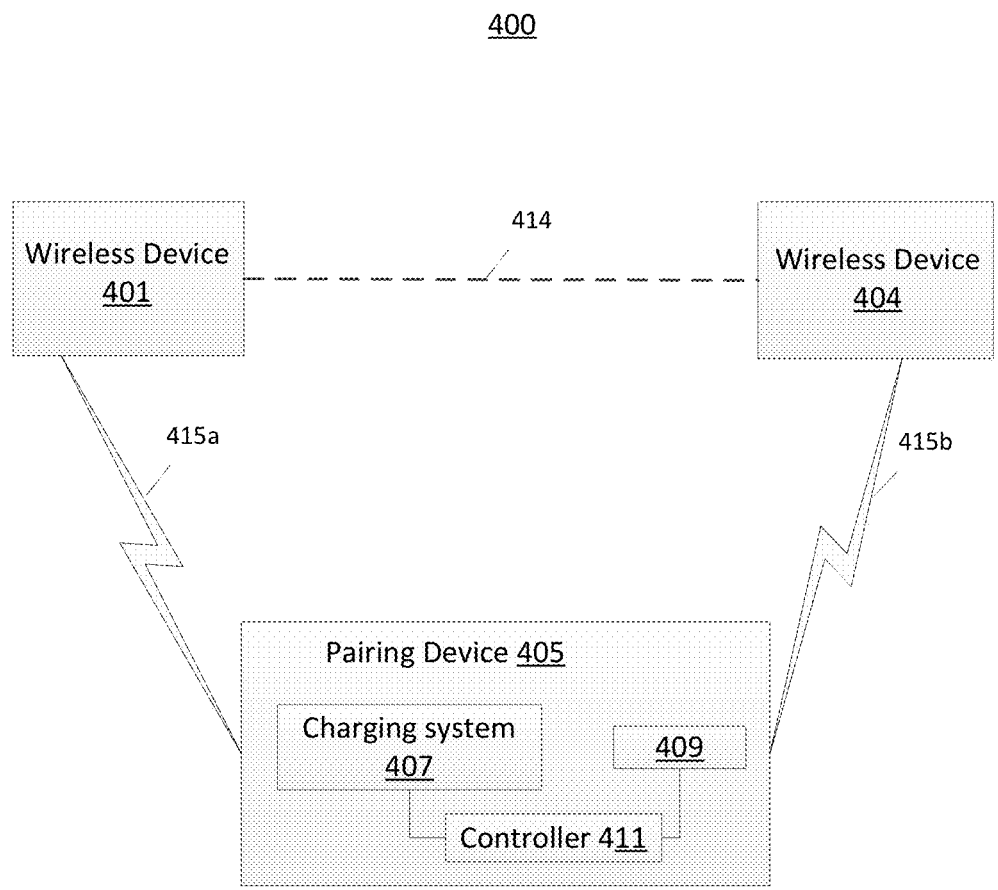
FIG. 4 depicts a device for pairing and charging other devices configured according to an implementation of a system that pairs at least two devices into a wireless network.

FIG. 4 depicts a device for pairing and charging devices in a wireless system according to an implementation. System 400 includes wireless devices 401 and 404 and pairing device 405. In some implementations, one or more of wireless devices 401 and 404 may be a medical device such as an electro-stimulation device, a TENS device, a therapeutic ultrasound device, a remote control, an imaging ultrasound device, or a laser device. In other implementation, one or more of wireless devices 401 and 404 may have a user interface. In other implementations, the user interface may be embedded in another device. Pairing device 405 may contain charging system 407, communication system 409 and controller 411. Charging system 407 may provide power to wireless devices 401 and 404. Communication system 409 may be configured with circuitry to communicate with other devices like, for example, devices 401 and 404. Controller 411 may contain a microprocessor (not shown) to process, read, store, or modify data or instructions between the components of system 400.

Figure 5:
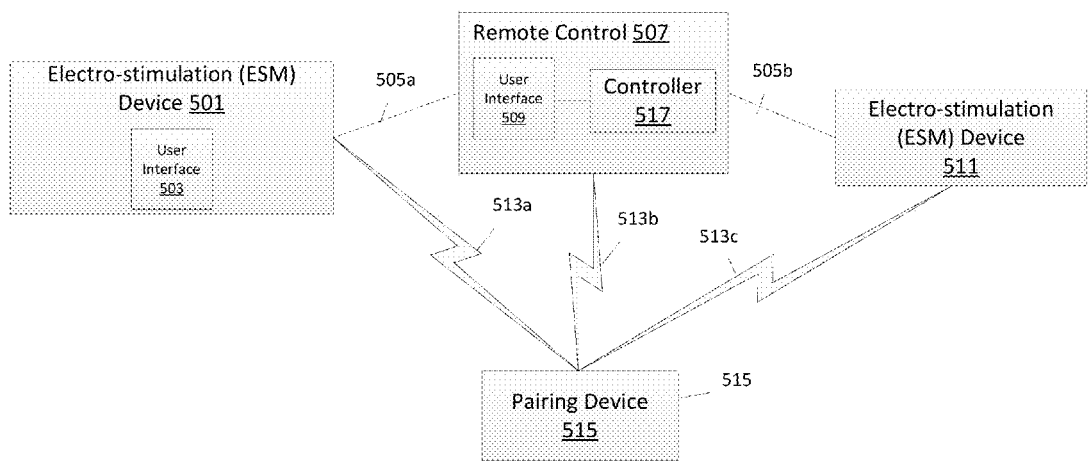
FIG. 5 depicts electro-stimulation devices and a remote control device configured to pair at least two devices into a wireless network.

FIG. 5 depicts electro-stimulation devices 501 and 511 and remote control 507 configured according to an implementation of a system. System 500 may contain electro-stimulation (ESM) devices 501 and 511, remote control 507 and pairing device 515. Remote control 507 may control EMS devices 501 and 511. EMS device 501 could contain a user interface 503, which, in part, displays visual output from EMS device 501. Electro-stimulation device 511 may not directly contain a user interface. Remote control 507 may contain user interface 509 and controller 517. User interface 509 may display visual output from remote control 507. In some implementations, user interface 509 may visual output from both remote control 507 and ESM device 511.

Figure 6A:
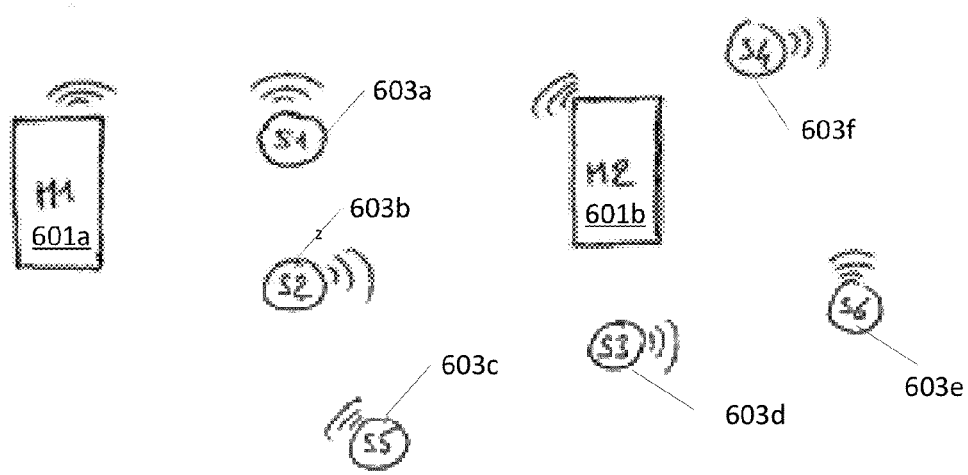
FIGS. 6A-6C depict a set of master devices and a set of slave devices configured according to an implementation of a system that pairs at least two devices into a wireless network.
Figure 6B:
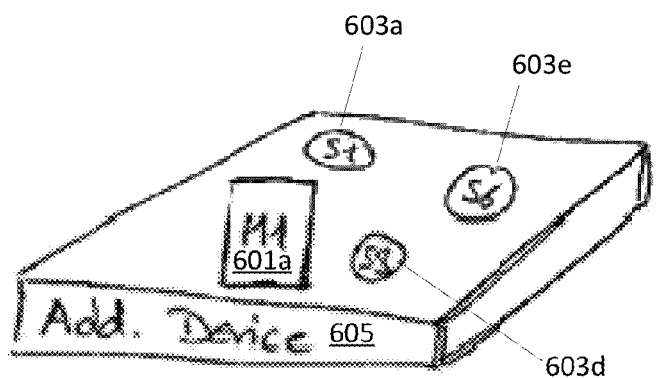
Figure 6C:
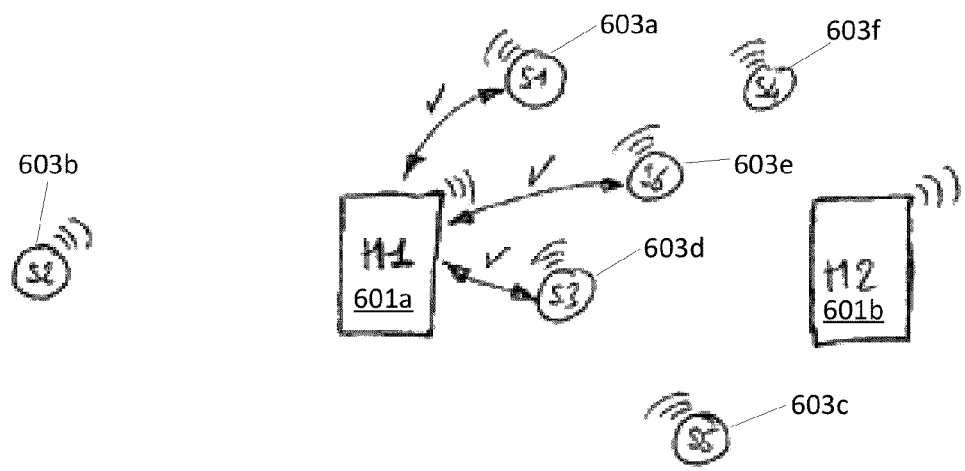

FIGS. 6A-6C depict a set of master devices and a set of slave devices configured according to an implementation of a system that pairs at least two devices into a wireless network.

FIG. 6A shows a set of electro-stimulation controllers 601 and a set of stimulation devices 603a, 603b, 603c, 603d, 603e. Electro-stimulation controllers 601 control stimulation devices 603a, 603b, 603c, 603d, 603e. For example, controller 601 may send instructions to stimulations devices 603 for providing electrical stimulation to a user. In some implementations, controllers 601 and stimulation devices 603 are enabled with wireless communication but are prevented from communicating with each other because they have not been paired into a wireless family network.

FIG. 6B depicts a set of electro-stimulation controllers 601, a set of stimulation devices 603a, 603d, and 603e, and pairing device 605. In some implementations, controllers 601 and devices 603 are placed in proximity to pairing device 605. Pairing device 605 many communicate with each controller 601 and each stimulation device 603a, 603d, and 603e that lie in contact or within proximity to pairing device 605. Pairing device 605 may pair controller 601a and the devices 603a, 603c, and 603e, which lie within the proximity threshold, into a wireless family. Once in a wireless family, controller 601a and device 603a, 603d, and 603e may communicate with each other and recognize the existence of other components in the family. In some implementations the proximity threshold may be physical contact, electrical contact, a distance that allows wireless communication, or may be any suitable means of recognizing the proximity of other devices such as 601 and 603. In some implementations, pairing device 605 recognizes the presence of the other devices without any additional action from a user. In other implementations, pairing device 605 may have an actuator, which may be a button a touch screen or any other suitable user input device. The actuator may, in part, initialize the pairing process.

FIG. 6C shows a subset of electro-stimulation remote controllers 601 and a subset of stimulation devices 603 being paired into a network. Controller 601a and the devices 603a, 603c, and 603e remain connected within the same wireless family after being removed from the within the proximity threshold of pairing device 605. Controller 601b and devices 603b, 603d, and 603f were not placed within the proximity threshold of pairing device 605 and therefore are not in the same wireless family and are not recognized by the wireless family do not communicate with other devices in the wireless family.

Figure 7A:
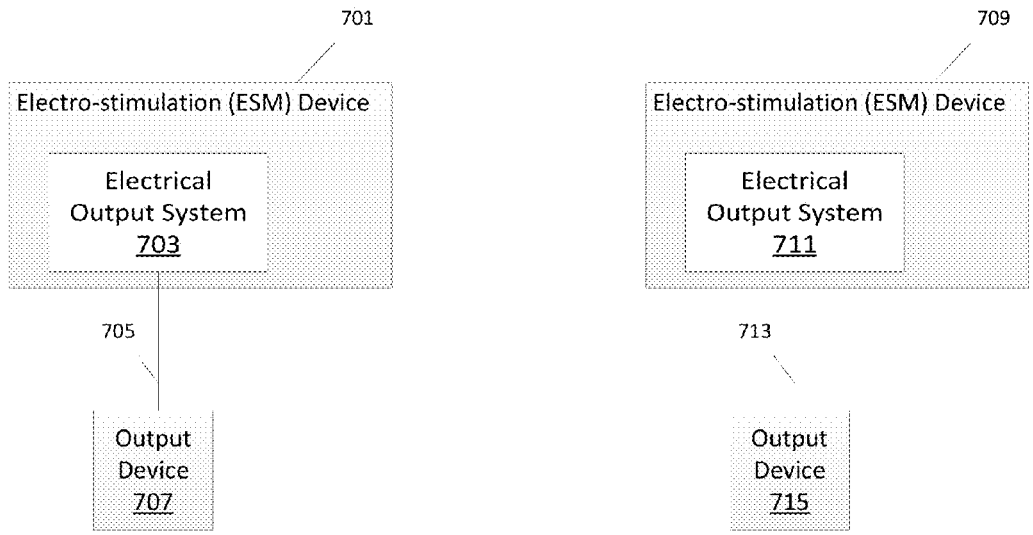
FIG. 7A depicts the structure of electro-stimulation (ESM) device, each including a stimulation output system.

FIG. 7A depicts the structure of electro-stimulation (ESM) devices configured according to in one implementation of the system that transfers data between two or more medical devices. ESM device 701 may include electrical output system 703. Similarly, ESM device 709 may include electrical output system 711. ESM device 701 and ESM device 709 may be configured, respectively, to provide an electrical output from electrical output system 703 and 711 through electrical links 705 and 713 to output devices 707 and 715. The electrical output for device 710 and 709 may be electro-stimulation signals. For example, devices 701 and 709 may be electrotherapy units (e.g. for TENS or sports therapy) that provide electrical stimulation to the tissue of the user.

Figure 7B:
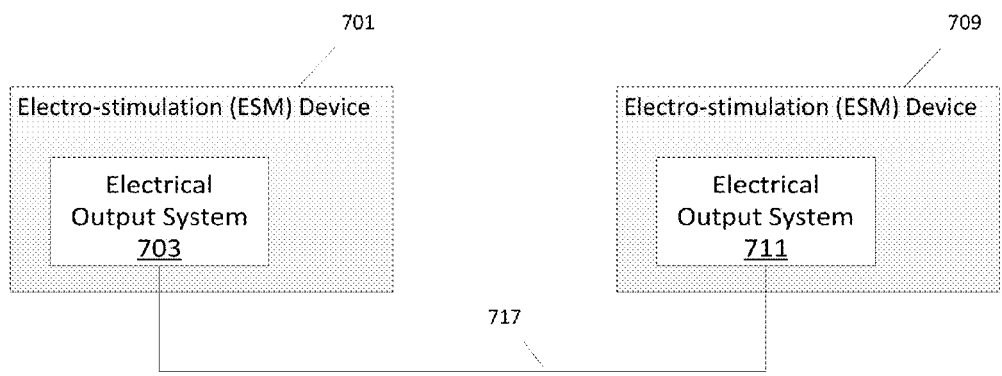
FIG. 7B depicts the structure of electro-stimulation (ESM) devices configured according to an implementation of a system that transfers data between two or more medical devices.

FIG. 7B depicts the structure of electro-stimulation (ESM) devices of FIG. 7A configured to transfer data between two or more medical devices. In one implementation, the ESM device 701 includes an electrical output system 703 and is configured to send or to receive an electrical signal from ESM device 709 to the electrical output system 711 of ESM device 709. Electrical output system 703 may send a signal through data transfer link 717 to electrical output system 711. Conversely, electrical output system 711 may send a signal through data transfer link 717 to electrical output system 703. Thus, the same electrical output 703 and 711 used for outputting electro-stimulation signals may also be used for sending and receiving data.

In some implementations, the signal sent through data transfer link 717 may travel only in one direction: either from electrical output system 703 to electrical output system 711, or from electrical output system 711 to electrical output system 703. In other implementations, the signal travels in both directions. The signal sent through data transfer link 717 may transfer data, indicate the occurrence of an event, contain a message, transfer medical device usage and compliance data, or implement security protocols between ESM devices 701 and 709.

In FIG. 7A electrical output system 703 is depicted in a configuration for providing an electrical output to output device 707. In FIG. 7B, the same electrical output system 703 is depicted in a configuration for sending a signal to or for receiving a signal from electrical output system 711.

Figure 8A:
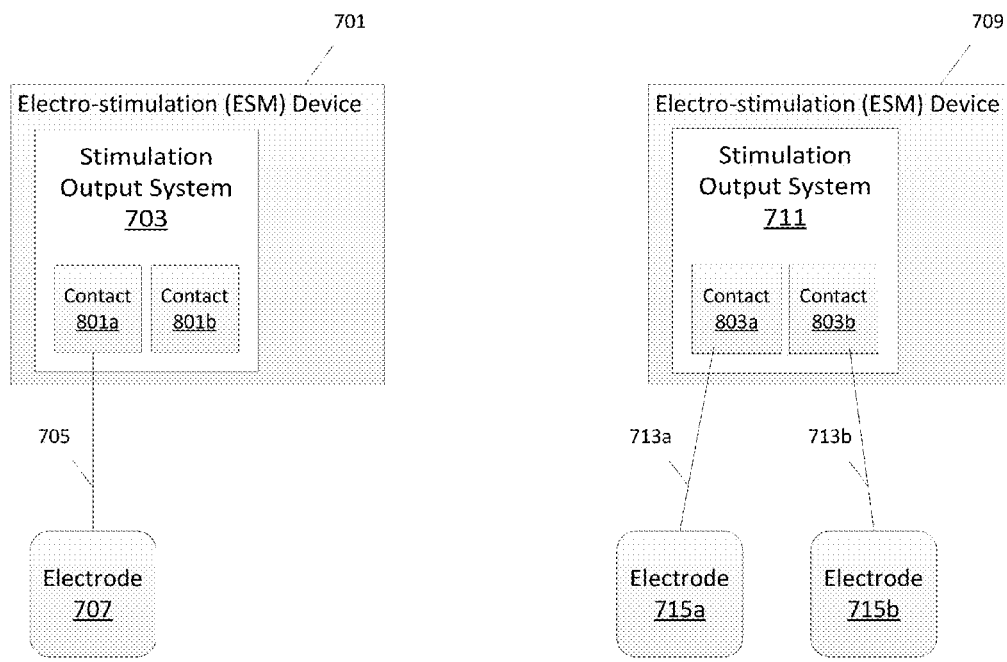
FIG. 8A depicts the structure of electro-stimulation (ESM) devices, each including a stimulation output system with at least one contact.

FIG. 8A depicts the structure of the electro-stimulation (ESM) devices of FIG. 7, configured to transfer data between two or more medical devices. In the illustrated implementation, ESM device 701 contains an electrical output system that is also a stimulation output system 703, and contains two contacts electrical 810a and 801b. The contacts are connected by electrical link to an electrical output device which may be an electrode 707b for providing electrical stimulation to the tissue of a user. Stimulation output system 703 sends a signal from contact 801a through the electrical link 705 and electrode 707. ESM Device 701 provides stimulation through one electrode 707 while ESM device 709 sends and receives stimulation to and from the two electrodes 715a and 715b. Electrodes 707, 715a and 715b could each be attached to a person, in part, to provide a therapeutic signal to the person's body. For example, the electrodes 707, 715a and 715b may be attached to the surface of a patient's body or may be implanted subcutaneously.

In addition, FIG. 8A depicts electrical output systems 703 and 711 each having two contacts 801 and 803. In some implementations, electrical output systems 703 and 711 each contain one or more contacts 801 and 803 respectively. In some implementations, electrodes 707, 715a and 715b are connected to a single person. In other implementations, electrode 707 is connected to one person while electrodes 715a and 715b are connected to another person. In still other implementations, electrode 715a is connected to one person while electrode 715b is connected to different person. Electrical links 705, 713a and 713b may be a wired connection such as a metal wire, a copper wire or any electrically conductive material. However, in other implementations electrical links 705, 713a and 713b includes a wireless connection.

Figure 8B:
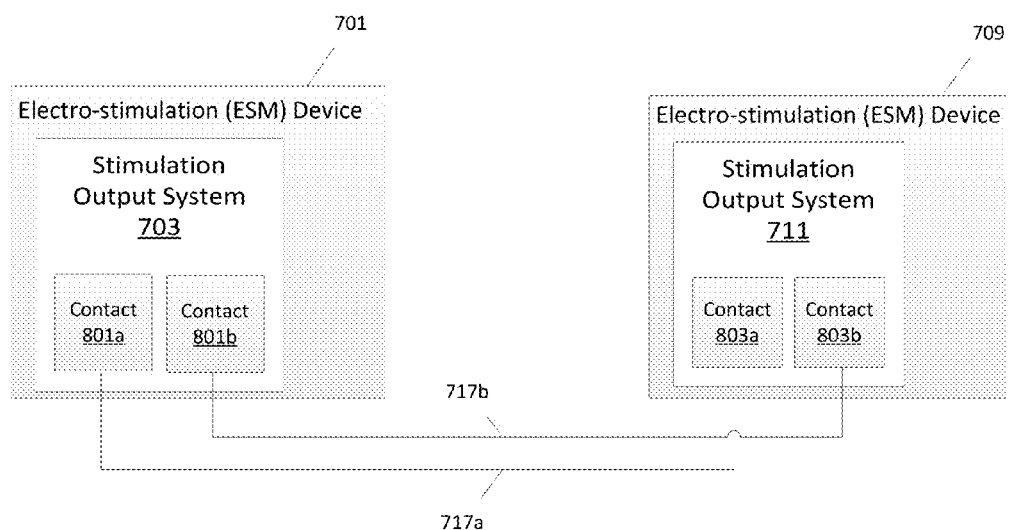
FIG. 8B depicts the structure of electro-stimulation (ESM) devices, each including a stimulation output system with at least one contact, configured according to an implementation of a system that transfers data between two or more medical devices.

FIG. 8B depicts the structure of the electro-stimulation (ESM) devices of FIGS. 7 and 8A, configured according to one implementation of the system that transfers data between two or more medical devices. In one implementation, the ESM device 701 may be configured to send a signal to or to receive a signal from ESM device 709. A signal may transfer between EMS device 701 and ESM device 709 by ESM device 701 generating a signal in the stimulation output system 703, stimulation output system 703 sending the signal from contact 801a though transfer link 717a to contact 803a contained in ESM device 709, thereby completing the transfer from EMS device 701 to ESM device 709. A similar path may exist between contact 801b through transfer link 717b to contact 803b. In some implementations, signals may transfer in both directions between ESM devices 701 and 709. In other implementations the signal may travel in one direction.

Turning to both FIGS. 8A and 8B, in FIG. 8A ESM device 709 having electrical output system 711 is depicted in a configuration for providing an electrical output to electrodes 715. In FIG. 8B, the same ESM device 709 having the same electrical output system 711 is depicted in a configuration for sending to or for receiving a signal from ESM device 707 having electrical output system 703.

Figure 9A:
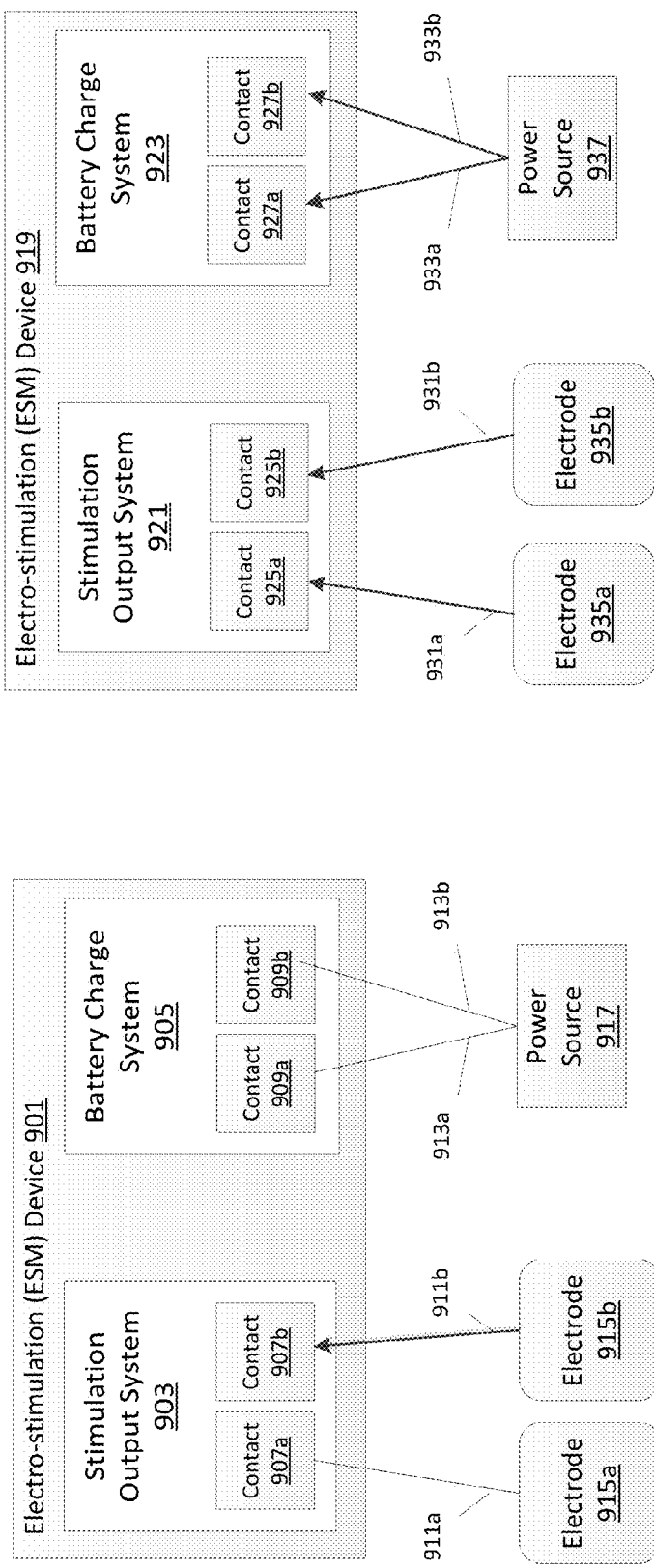
FIG. 9A depicts electro-stimulation (ESM) devices, each including a stimulation output system and a battery charge input system.

FIG. 9A depicts electro-stimulation (ESM) devices, each device having a stimulation system and a battery charging system. ESM device 901 may contain stimulation output system 903 and battery charging system 905. Stimulation output system 903 may contain two contacts 907a and 907b. ESM device 901 may also be attached to one or more electrodes 915 by an electrical links 911. ESM device 901 may implement electro-stimulation therapy by generating an electrical signal in stimulation output system 903, sending the signal from contacts 907 through electrical links 911 to electrodes 915, thereby providing an electro-stimulation therapy. Battery charge system 905 may contain two contacts 909a and 909b. ESM device 901 may receive power from the power source 917 through power source 917 generating power, power source 917 sending power through power links 913, and ESM device 901 receiving power at contacts 909 into battery charge system 905. ESM device 919 may contain similar components and operate in a manner similar to ESM device 901.

Figure 9B:
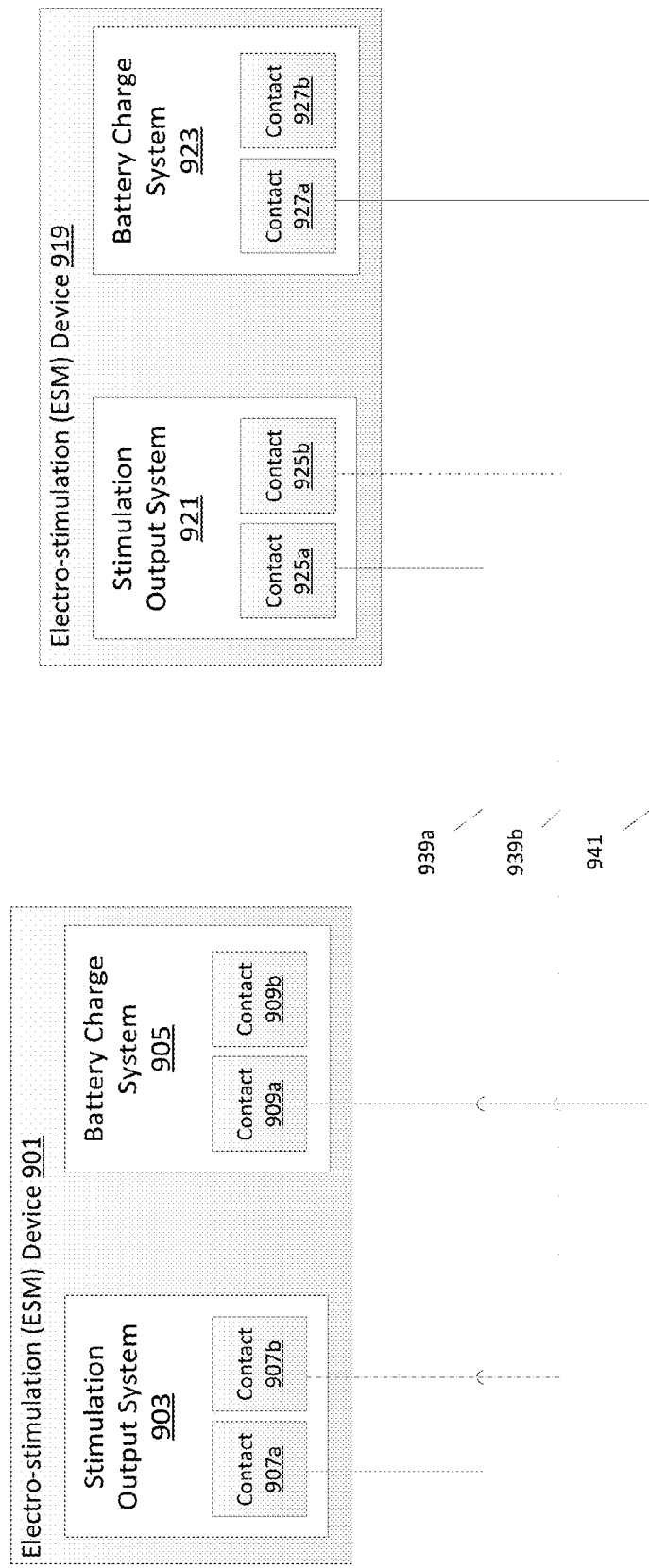
FIG. 9B depicts an electro-stimulation (ESM) devices, including a stimulation output system and a battery charge input system, configured according to an implementation of a system that transfers data between two or more medical devices.

FIG. 9B depicts the electro-stimulation (ESM) devices of 9A, configured to transfer data between two or more medical devices. In one implementation, ESM device 901 may be configured to send a signal to or to receive a signal from ESM device 919 by using one or more transfer links 939 and a ground link 941. A signal may transfer between EMS device 901 and ESM device 919 by, in part, ESM device 919 generating a signal in the stimulation output system 921, stimulation output system 921 sending the signal from contact 925a though transfer link 939a to contact 907a contained in ESM device 901, thereby completing the transfer from EMS device 901 to ESM device 919. Ground link 941 is used as a ground wire during signal transfer. In some implementations, a similar path for sending a signal between EMS device 901 and ESM device 919 may exist between contact 925b thorough transfer link 939b to contact 907b. In some implementations, signals may transfer in both directions between ESM devices 901 and 919. In other implementations the signal may travel in one direction.

Figure 10B:
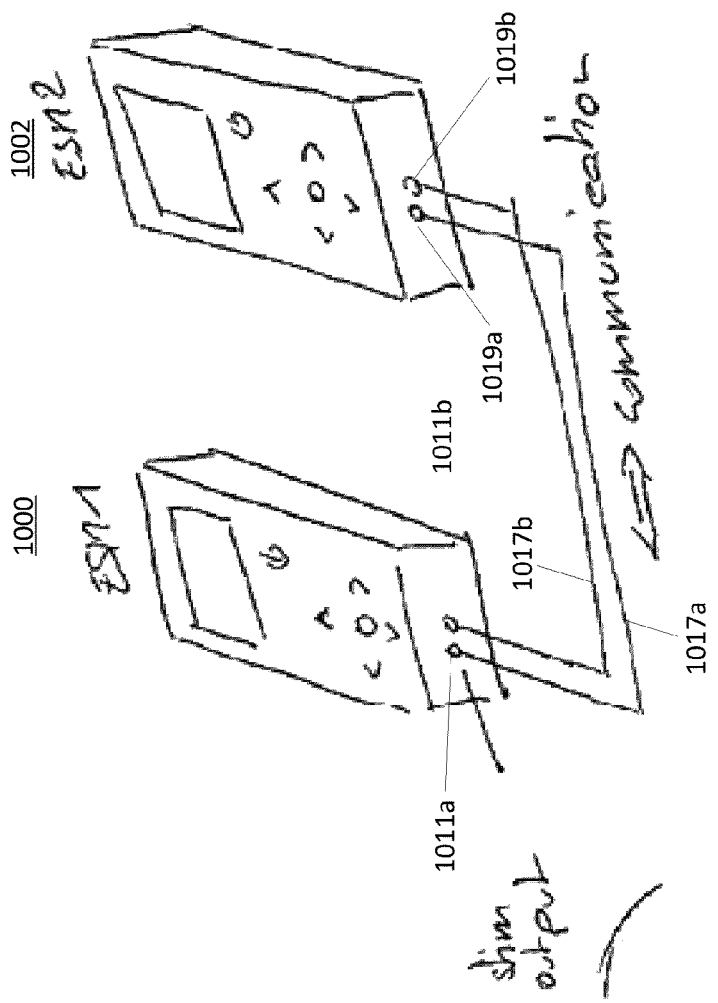
FIG. 10B depicts electro-stimulation (ESM) devices configured according to an implementation of a system that transfers data between two or more medical devices.
Figure 10A:
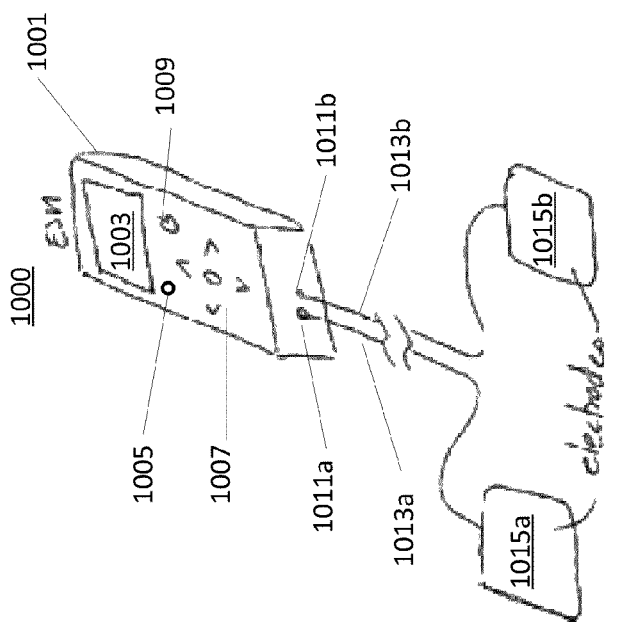
FIG. 10A depicts an electro-stimulation (ESM) device including a stimulation output system.

FIG. 10A depicts an electro-stimulation (ESM) device 1000 configured according to one implementation. ESM device 1000 contains housing 1001, display 1003, power button 1009, actuator 1005, input panel 1007, electro-stimulation contacts 1011a and 1011b, wires 1013a and 1013b and electrodes 1015a and 1015b connected to contacts 1011 via wires 1013. Housing 1001 may protect the electrical systems contained in the device and provide structure to support display 1003, power button 1009, actuator 1005, input panel 1007, and electro-stimulation contacts 1011. Display 1003 may to provide visual output from the ESM device 1000 to a user. Power button 1009 may activate or deactivate ESM device 1000. Actuator 1005 may be used to initiate a signal transfer from the device through contacts 1011. Input panel 1007 may allow a user to input, modify, or retrieve data from ESM device 1000. In some implementations, a user may control electrotherapy using input panel 1007. Electro-stimulation contacts 1011 may be an electrically conductive contact point, which may also be used to send an electro-therapy signal from ESM device 1000 to another device such as electrode 1015. Wires 1013 may conduct electrical signals from electro-stimulation contacts 1011 to electrodes 1015. In some implementation, electrodes 1015 are connected to the body of a patient to provide electro-stimulation therapy to the tissue of the patient.

FIG. 10B depicts the electro-stimulation (ESM) devices of FIG. 10A configured according to one implementation of the system. ESM device 1000 and ESM device 1002 are connected at their respective electro-stimulation contacts 1011 and 1019 by wires 1017. In some implementations the wires 1017 are, in part, an electrically conductive material, which allows the ESM device 1000 to send signals to and receive signals from ESM device 1002, thereby allowing data transfer between the devices. Actuator 1005 may initiate a signal transfer from the ESM device 1000 to ESM device 1002. Comparing FIGS. 10A and 10B, the same electro-stimulation contacts 1011 may be used to provide both electro-stimulation therapy and to transfer data to one or more devices.

FIG. 11A depicts an electro-stimulation (ESM) device having a stimulation output system and a battery charge input system. ESM device 1100 may contain housing 1101, display 1103, power button 1109, actuator 1105, input panel 1107, electro-stimulation contacts 1111, and battery charge contacts 1113. In FIG. 11A, electro-stimulation contacts 1111a and 1111b include ground contact 1113a. Housing 1001 may protect the electrical systems contained in the device and provide structure to support display 1003, power button 1109, actuator 1105, input panel 1107, and electro-stimulation contacts 1111. Display 1103 may to provide visual output from the ESM device 1100 to a user. Power button 1109 may activate or deactivate ESM device 1100. Actuator 1105 could initiate a signal transfer from the device through contacts 1101 to another device (not shown). Input panel 1107 may allow a user to input, modify, or retrieve data from ESM device 1000. Electro-stimulation contacts 1111 may be an electrically conductive contact point, which may be used to send an electronic signal from ESM device 1100 to another device such as electrode (not shown). Battery charge contacts 1113 may be an electrically conductive contact point, which may be used to provide power to ESM device 1100.

FIG. 11B depicts electro-stimulation (ESM) devices, each having a stimulation output system and a battery charge input system, according to one implementation of the system that transfers data between two or more medical devices. ESM device 1100 and ESM device 1102 may be connected at their respective electro-stimulation contacts 1111 and 1019 by one or more wires 1017. In addition, ESM device 1100 and ESM device 1102 may be connected at their respective battery charge contacts 1113 and 1119 by one or more wires 1121. In some implementations, one or more wires 1117 are, in part, allow ESM device 1100 to send signals to and receive signals from ESM device 1102 while using the wire 1121 as a ground wire. A signal may transfer between EMS device 1100 and ESM device 1102 by, in part, sending a signal from electro-stimulation contact 1111b though transfer link 1117b to electro-stimulation contact 1119b contained in ESM device 1102, thereby completing the data transfer from EMS device 1100 to ESM device 1102. Wire 1121 may be used as a ground wire during the transfer. Actuator 1105 may initiate a signal transfer from the ESM device 1100 to ESM device 1102.

Comparing FIGS. 11A and 11B, the same electro-stimulation contacts 1011 may be used to provide electro-stimulation therapy from a device and to provide data transfer between two or more devices. Similarly, the same battery charge contacts 1113 may be used to provide power to a device and to a ground during data transfer between two or more devices.

Figure 12:
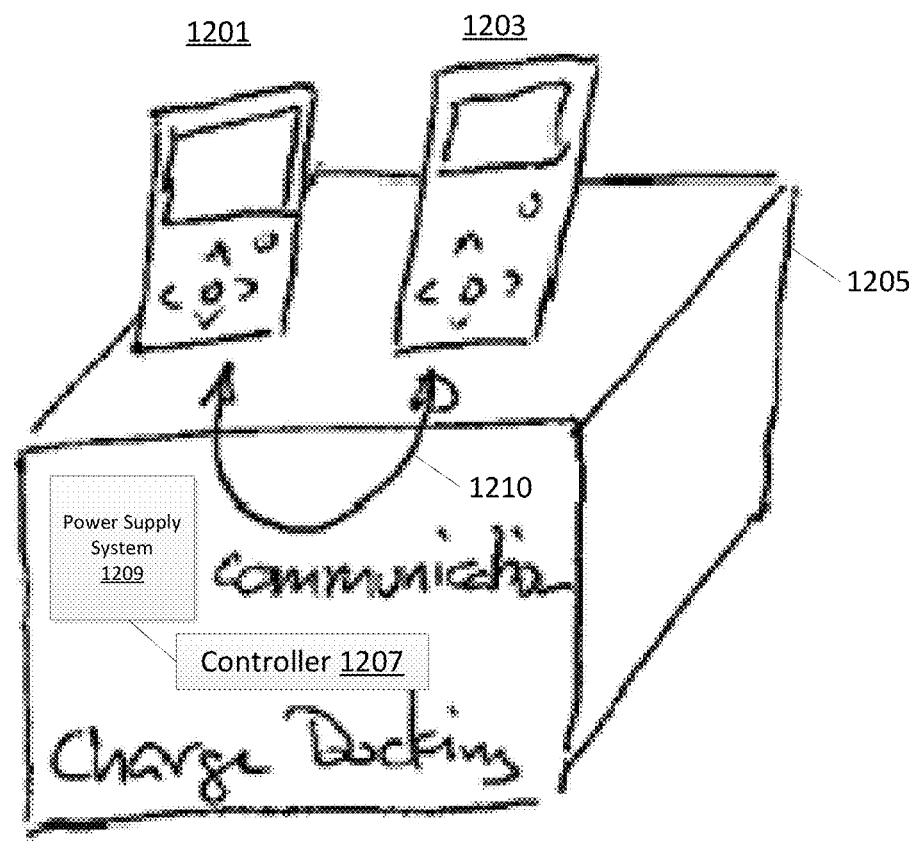
FIG. 12 depicts electro-stimulation (ESM) devices and a charging dock configured according to an implementation of a system that transfers data between two or more medical devices.

FIG. 12 depicts electro-stimulation (ESM) devices and a charging dock configured according to one implementation of the system that transfers data between two or more medical devices. System 1200 includes charging dock 1205, electro-stimulation devices 1201, and electro-stimulation device 1203. Charging dock 1205 includes controller 1207 and power system 1209. Controller 1207 may contain a microprocessor (not shown) to process, read, store, or modify data or instructions between the components of system 1200. Power system 1209 may provide power to medical devices 1201 and 1203 and, in part, provide communication 1210 between electro-stimulation devices 1201 and 1203.

Figure 13:
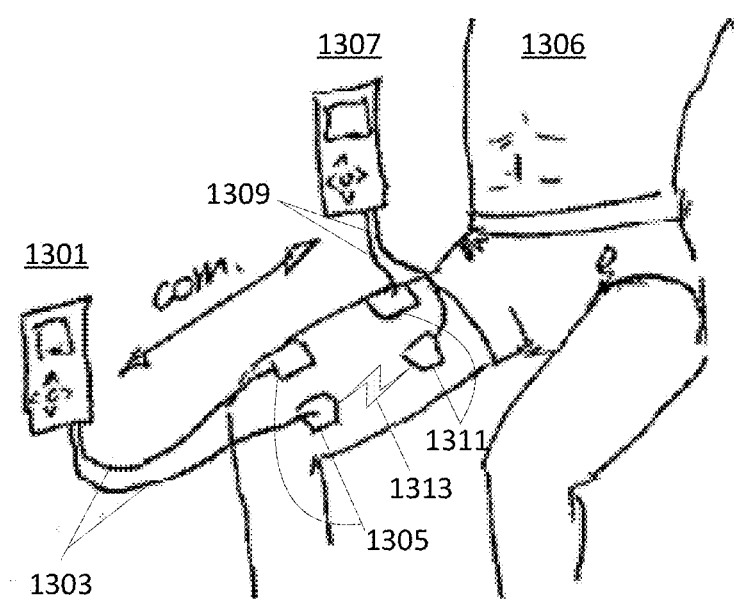
FIG. 13 depicts electro-stimulation (ESM) devices in contact with a body according to an implementation of a system.

FIG. 13 depicts electro-stimulation (ESM) devices 1301 and 1307 in electrical contact with a patient's. ESM devices 1301 and 1307 are connected to patient 1306. ESM devices 1301 and 1307 are connected to one end of wires 1303 and 1309 and another end of wires 1303 and 1309 are connected to electrodes 1305 and 1311, respectively. Electrodes 1305 and 1311 may be placed in contact with the patient's skin to provide electro-stimulation therapy to the patient's tissue. ESM devices 1301 and 1307 may also communicated data to each other through the tissue of patient 1306, to communicate 1313 between the devices through the patient's skin, or to both provide therapy an communicate 1313 simultaneously through the patient's skin.

Figure 14:
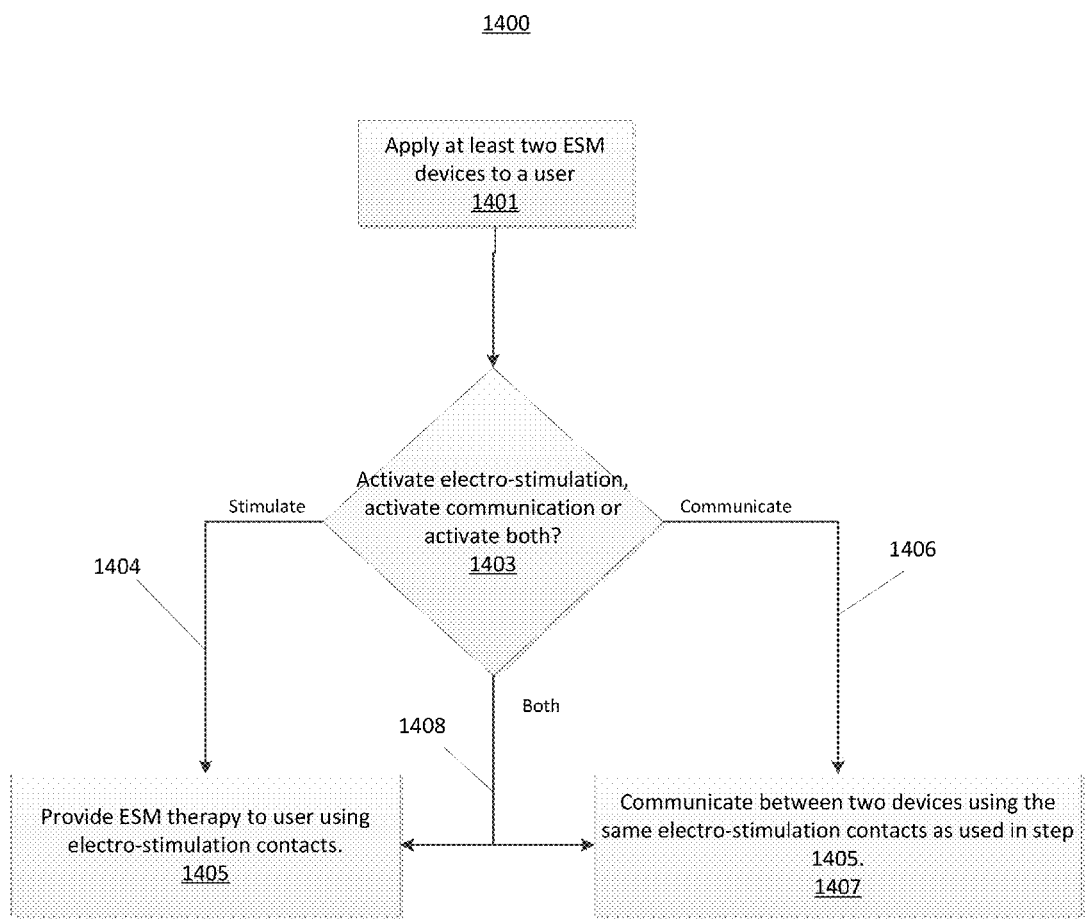
FIG. 14 illustrates a method for transferring data between two or more medical devices.

FIG. 14 illustrates one implementation of a method for transferring data between two or more medical devices. Method 1400 includes step 1401 applying at least two electro-stimulation devices to a user; step 1403 activating the electro-stimulation 1404, activating communication between the at least two electro-stimulation devices 1406, or activating both stimulation and communication simultaneously 1408; step 1405 providing ESM therapy to user using electro-stimulation contacts; and step 1407 communicate between two devices using the same electro-stimulation contacts as used in step 1405. In some implementations, step 1401 may apply to another medical device that is not an electro-stimulation device.

It is to be understood that the foregoing description is merely illustrative, and is not to be limited to the details given herein. While several implementations have been provided in the present disclosure, it should be understood that the disclosed systems, devices and methods and their components may be embodied in many other specific forms without departing from the scope of the disclosure.

Variations and modifications will occur to those of skill in the art after reviewing this disclosure, where disclosed features may be implemented in any combination and subcombinations (including multiple dependent combinations and subcombinations), with one or more other features described herein. The various features described or illustrated above, including any components thereof, may be combined or integrated in other systems; moreover, certain features may be omitted or not implemented.

Examples of changes, substitutions and alterations are ascertainable by one skilled in the art and to be made without departing from the scope of the information disclosed herein. All references cited herein are incorporated by reference in their entirety and made part of this application.

What is claimed is:

1. A system comprising:
at least two electronic devices, each of the at least two electronic devices having a unique ID, and at least one of the electronic devices being configured to communicate wirelessly with at least one of the other electronic devices only when the at least two electronic devices have been grouped into a wireless network; and
an additional device configured to wirelessly detect the presence of, communicate with, and distinctly identify each of the at least two electronic devices, the additional device being further configured to communicate the unique ID from each one of the at least two electronic devices to the other electronic devices of the at least two electronic devices to group the at least two devices into a wireless network when the at least two electronic devices are detected by the additional device to be located within a proximity threshold of the additional device,
the at least two electronic devices further configured to wirelessly communicate directly with each other only after being grouped into a wireless network by the additional device, direct wireless communications between the at least two electronic devices not going through the additional device.

2. The system of claim 1, wherein the additional device is a charging station.

3. The system of claim 1, wherein the wireless network is composed of one master and a slave.

4. The system of claim 1, wherein the communication between the additional device and the at least two devices is made though wireless communication.

5. The system of claim 4, wherein the wireless communication is a magnetic coupling.

6. The system of claim 4, wherein the wireless communication is Radio Frequency.

7. The system of claim 1, wherein the additional device recognizes the presence of the other devices within the proximity threshold with an additional action from a user.

8. The system of claim 7, wherein the user action is an action on an actuator.

9. The system of claim 8, wherein the actuator is a button.

10. The system of claim 1, wherein the grouping of the at least two devices into a wireless network is not initiated by a user action other than placing the at least two electronic devices within the proximity threshold of the additional device.

11. The system of claim 1, wherein one of the at least two devices is an electro-stimulator device.

12. The system of claim 1, wherein one of the at least two devices is a therapeutic ultrasound device.

13. The system of claim 1, wherein one of the at least two devices is an imaging ultrasound device.

14. The system of claim 1, wherein one of the at least two devices is a laser device.

15. The system of claim 1, wherein a user interface is embedded in another device.

16. The system of claim 1, wherein the grouping the at least two devices into a wireless network remains permanent until another grouping process is initiated by a user.

17. The system of claim 1, wherein the additional device is configured to detect the presence of the at least two electronic devices without any action from a user other than placing the at least two electronic devices within the proximity threshold of the additional device.

18. The system of claim 1, wherein the proximity threshold of the additional device requires that the at least two electronic devices be placed in physical contact with the additional device.

19. The system of claim 1, wherein the additional determines which of the at least two electronic devices to group into a wireless network according to the unique IDs of the at least two electronic devices.

20. A system comprising:
at least two electronic devices configured to wirelessly communicate directly with each other only if grouped into a wireless network,
an additional device configured to recognize the at least two electronic devices and group the at least two electronic devices into a wireless network when the at least two electronic devices are brought within a proximity threshold of the additional device, wherein the at least two electronic devices are further configured to wirelessly communicate directly with each other, after they are grouped by the additional device, such that direct wireless communications between the at least two electronic devices do not go through the additional device.

* * * * *